United States Patent
Ghosh et al.

(10) Patent No.: US 12,412,658 B2
(45) Date of Patent: Sep. 9, 2025

(54) AI BASED CONTEXT AWARE MULTIDIRECTIONAL PATIENT MOVEMENT

(71) Applicant: International Business Machines Corporation, Armonk, NY (US)

(72) Inventors: Partho Ghosh, Kolkata (IN); Akash U. Dhoot, Pune (IN); Shailendra Moyal, Pune (IN); Lakshmojee Rao Vulli, Bangalore (IN)

(73) Assignee: International Business Machines Corporation, Armonk, NY (US)

(*) Notice: Subject to any disclaimer, the term of this patent is extended or adjusted under 35 U.S.C. 154(b) by 742 days.

(21) Appl. No.: 17/524,352

(22) Filed: Nov. 11, 2021

(65) Prior Publication Data

US 2023/0145268 A1 May 11, 2023

(51) Int. Cl.
*G16H 40/67* (2018.01)
*G16H 10/60* (2018.01)

(52) U.S. Cl.
CPC ............ *G16H 40/67* (2018.01); *G16H 10/60* (2018.01)

(58) Field of Classification Search
None
See application file for complete search history.

(56) References Cited

U.S. PATENT DOCUMENTS

| | | |
|---|---|---|
| 5,054,140 A | 10/1991 | Bingham |
| 8,620,682 B2 | 12/2013 | Bechtel |
| 2014/0090173 A1 | 4/2014 | Dimaio |
| 2016/0278692 A1* | 9/2016 | Larson .............. A61B 5/0205 |
| 2018/0214091 A1 | 8/2018 | Baker |
| 2019/0005195 A1 | 1/2019 | Peterson |
| 2019/0005200 A1 | 1/2019 | Zimmerman |
| 2019/0103182 A1* | 4/2019 | Borshch ............ G06F 16/24575 |
| 2022/0087617 A1* | 3/2022 | Main ................... G16H 50/20 |

FOREIGN PATENT DOCUMENTS

| | | |
|---|---|---|
| CN | 109979587 A | 7/2019 |
| CN | 110709938 A | 1/2020 |
| CN | 113143658 A | 7/2021 |
| GB | 2102675 A | 2/1983 |
| WO | 8600221 W | 1/1986 |
| WO | 2020264140 A1 | 12/2020 |

(Continued)

OTHER PUBLICATIONS

International Search Report and Written Opinion, International Application No. PCT/CN2022/118966, International Filing Date Sep. 15, 2022.

(Continued)

*Primary Examiner* — Devin C Hein
(74) *Attorney, Agent, or Firm* — Monchai Chuaychoo

(57) ABSTRACT

An approach for providing movement settings for a smart bed associated with an immobile patient is disclosed. The approach includes retrieving patient data and retrieving environmental data. The approach analyses patient profile and creates a digital twin of patient. In the digital twin environment, the approach models the patient movement and send patient movement setting based on desired outcome. Finally, the approach sends instructions to the smart patient bed.

20 Claims, 4 Drawing Sheets

(56) References Cited

FOREIGN PATENT DOCUMENTS

WO 2023/082832 A1 5/2023

OTHER PUBLICATIONS

"Vibrating Surface for Person Repositioning and Transferring", An IP.com Prior Art Database Technical Disclosure, Authors et. al.: Disclosed Anonymously, IP.com No. IPCOM000187396D, IP.com Electronic Publication Date: Sep. 3, 2009, 8 pages.
Bandala et al., "Development and Design of Automated Hospital Bed with Incremental Panels for Bedsore Prevention", TENCON 2014, Oct. 2014, DOI:10.1109/TENCON.2014.7022411, 7 pages.
Basmajian, Arin, "Design of An Assist Device for Automated Rolling and Repositioning of Bedridden Patients", Submitted to the Department of Mechanical Engineering on May 6, 2002 in partial fulfillment of the requirements for the degree of Master of Science in Mechanical Engineering, 126 pages.

\* cited by examiner

AI BASED CONTEXT AWARE MULTIDIRECTIONAL PATIENT MOVEMENT

BACKGROUND

The present invention relates generally to the field of healthcare, and more particularly to providing mobility assistance to patients.

Mobility means physical movement which includes both simple gross motor movements, complex fine motor movements and its corresponding movements and associations. Any condition, complete or partial, by birth or due to accident etc. that disrupts this integrated process can lead to impaired mobility or immobility.

Acutely immobile bed ridden patients do require assistive mobility for themselves for their daily activities. These activities can include eating meals, hygienic clean up, physical therapy, etc. Moving such patient within the bed requires an external support from a minimum of two to three persons, depending on the size and weight of the patient, the size and strength of the care providers. Patients who require this type of assistance are generally immobile or acutely ill and may be unable to assist with the any mobility such as paralytic, semi or complete comatose patients and/or acutely especially abled accessible person.

SUMMARY

Aspects of the present invention disclose a computer-implemented method, a computer system and computer program product for providing movement settings for a smart bed associated with an immobile patient. The computer implemented method may be implemented by one or more computer processors and may include, retrieving patient data associated with a patient; retrieving environmental and health data associated with the patient; analyzing patient profile associated with the patient; creating digital twin version of the patient; modeling patient movement based on the digital twin version of the patient; retrieving patient movement setting from the digital twin version of the patient; and instructing a patient bed.

According to another embodiment of the present invention, there is provided a computer system. The computer system comprises a processing unit; and a memory coupled to the processing unit and storing instructions thereon. The instructions, when executed by the processing unit, perform acts of the method according to the embodiment of the present invention.

According to a yet further embodiment of the present invention, there is provided a computer program product being tangibly stored on a non-transient machine-readable medium and comprising machine-executable instructions. The instructions, when executed on a device, cause the device to perform acts of the method according to the embodiment of the present invention.

BRIEF DESCRIPTION OF THE DRAWINGS

Preferred embodiments of the present invention will now be described, by way of example only, with reference to the following drawings, in which.

DETAILED DESCRIPTION

Figure 1:
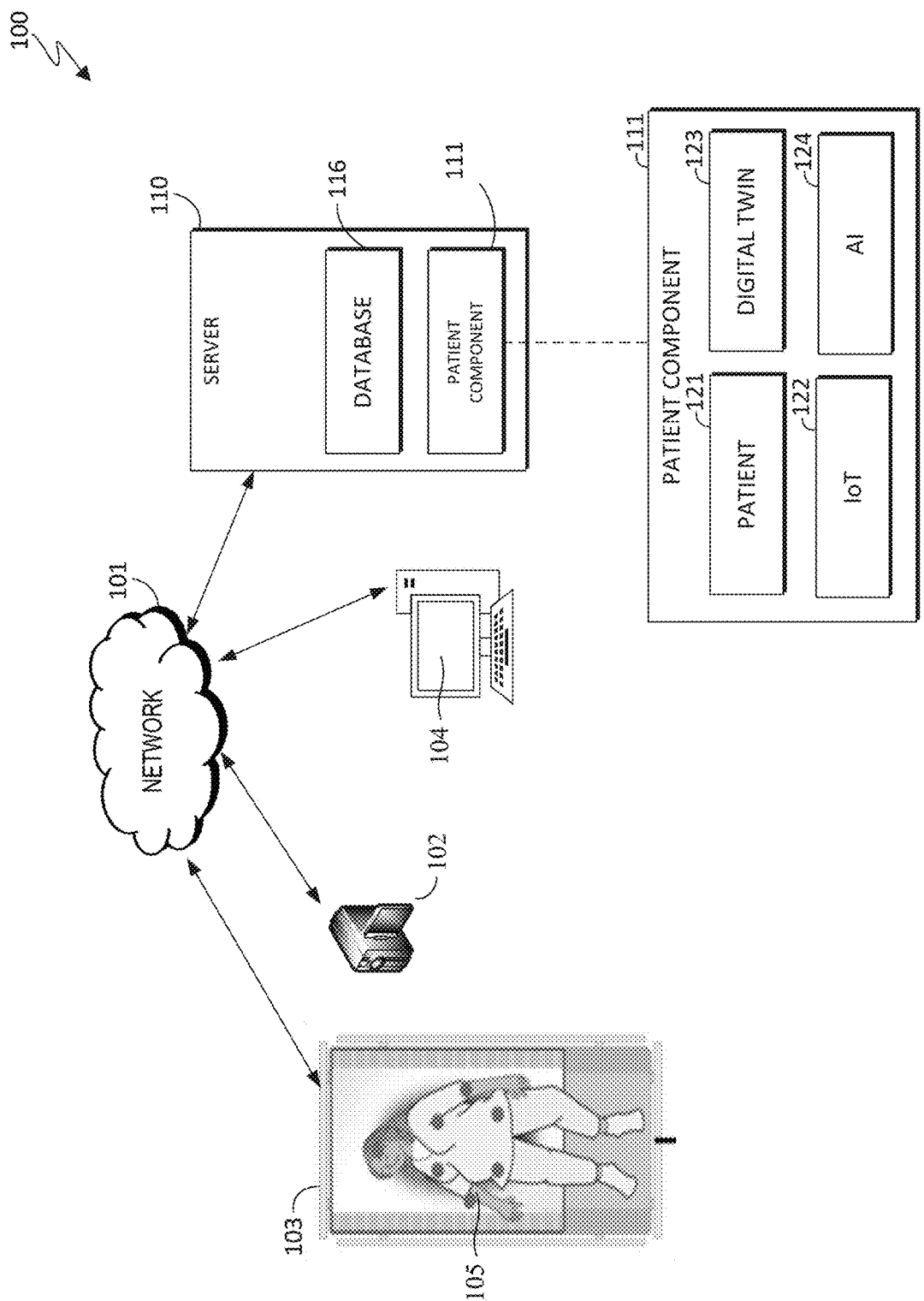
FIG. 1 is a functional block diagram illustrating a patient mobility environment, designated as 100, in accordance with an embodiment of the present invention.

The current state of art as it pertains immobile patient care, specifically with patient mobility can present some challenges. For example, one challenge involves moving an acutely immobile (i.e., bed ridden) patient may require dexterity and stability as not aggravate the current medical condition.

Embodiments of the present invention recognizes the deficiencies in the current state of art as it relates to providing mobility to immobile patient and provides an approach. One approach comprise of creating a patient rolling system which determines the need for patient positional adjustment based on the context, IoT (Internet of Things) sensor data and patient health conditions and thereby initiates dynamic three dimensional rolling profile for the patient with applied AI capabilities. The same approach may leverage the use of a digital twin technology to provide the optimal setting and recommendations to assist patients with mobility. Digital twin technology can be used to model of the patient body or part of the body. Using digital patient twin simulation of environmental and whether conditions, embodiment will be able to identify potential uncomfortable scenarios (skin irritants, frequent sweating, moist skin) generating a need of patient movement or re-adjustment to prevent the possible conditions.

What is digital twin computing? Digital twin computing technology leverages IoT, artificial intelligence (i.e., leveraging machine/deep learning) and software analytics to create living digital simulation models that update and change as their physical counterparts change. A digital twin continuously learns and updates itself to represent its near real-time status. A digital twin also integrates historical data from past usage to factor into its digital model. What is a simulation? A simulation is an approximation of a process and/or a system (e.g., machines, etc.). Furthermore, simulations are run in virtual environments that may be representations of physical environments but do not integrate real-time data (i.e., used by digital twin computing). The main difference between a simulation (and/or modeling) versus a digital twin is that a digital twin can use real-time data based on the regular transfer of information between the digital twin and its corresponding physical environment.

Some embodiments of the present invention can incorporate an E-Cloth, which is integrated system with various IoT devices like room sensors, smart watches, smart wearable, mobile devices and patient wearables. Embodiments of the present invention can gather information about patient health and pre-existing medical conditions from electronic medical records. Furthermore, Embodiments of the present invention can derive the various parameters using patient digital twin and from IoT devices like but not limited to, person, health parameters, body position, body mass, weight of the injured portion, comfort, etc.

Some embodiments of the present invention can leverage a smart bed can improve a user's sleep experience through the use of data from temperature, humidity, motion, and brainwave sensors. The smart bed may comprise of various sensors can provide patient beds with information to make real-time adjustments to a user's sleeping conditions that do not require the user to make any manual adjustments. Other smart beds, particularly hospital or nursing home beds, may comprise a sheet arranged between multiple rollers along the periphery of the patient wherein two opposite sides or end portions of the sheet each being wound around one of the two rollers of which each is associated with a drive means. Other data used by embodiment can include various environmental parameters and whether condition (odor, noise, light, moisture, temperature, etc.).

Some embodiments of the present invention allow rolling (i.e., three dimension) of the patient using multiple segmented rollers along the periphery of the bed wherein the segmented rollers will synchronously work to move portion of the e-cloth. Based on the context of rolling of the patient, the proposed system will enable the multi segmented roller collaborative rolling wherein one set of roller will dispatch e-cloth in an axial direction and another set of roller will retract the smart cloth in another axial direction. The bed comprises of rollers with electromotor drive means, serving to rotate the rollers to wind the sheet from one or plurality of rollers to the other plurality of rollers in either direction, particularly as to provide a turning of a person laying on the sheet.

Some embodiments may leverage an AI infused patient rolling system that will be able to generate a context for a need of patient movement. Embodiment can rely on the use of a simulation of digital twin of the patient and the environment IoT data wherein context can include, but it is not limited to, comfort, long hours in one position, non-compliance, or patient shift, contextual situation (type of and part of wound or infection or fracture, IV drip in hand etc.), type of injury and body portion. Embodiment can initiate a dynamic three dimensional rolling profile for the patient with applied AI capabilities. Furthermore, embodiment has the capability to determine a non-complaint position and degree of non-compliance of the patient. The rolling profile can include resetting the patient to its original position based on the patients auto sliding to another non-compliant position (ex: during an inclined lying condition).

Some embodiments uses multifarious IoT sensor data from smart wearables and e-cloth, the proposed system will dynamically be able to detect a condition for patient pressure ulcer, and thereby auto initiate the patient and/or portion of the patient's body movement by trigging of rolling for the segmented roller releasing e-cloth in an axial direction to relieve the pressure from an ulcer prone part of the patient's body.

Some embodiments can identify prolonged lying in one position for prolonged time period and will be able to dynamically change patient's lying profile to a secondary position using differential time based patient movement and auto triggering to a tertiary position an elapsed time frame. Based on potential condition of pressure ulcer in one or many portions of the body due to patient lying in one position for prolonged time period, the proposed system will be able to dynamically change patient's lying profile to a secondary position using differential time based patient movement and auto triggering to a tertiary position an elapsed time frame.

Some embodiments has the capability of auto initiates smart home based events to adjust the environmental conditions, such as, but it is not limited to, auto adjustment of the humidity and temptation, auto opening or closure of smart windows, auto dimming of bright light etc. thereby creating an environmental scenario comforting to the patient condition.

Some embodiments will be able to generate a position profiling based on time duration and auto initiate patient movement after the expiry of primary time duration and its corresponding position to a secondary position for a secondary time duration. Embodiment checks the movement accuracy based on patient weight etc. and thereby initiates an adjustment movement for any inaccurate positioning.

Some embodiments can identify potential pulmonary congestion due to mucus and/fluid buildup in chest for multifarious reasons like but too limited to bloating, overeating, inability to swallow, or pre-existing pulmonary conditions using IoT, smart wearable and Patient digital twin. Embodiment can autonomously adjust the positioning of the patient by dynamically setting the patient movement based on identification of potential pulmonary congestion conditions.

Some embodiments can create a classified corpus of contextual scenarios and correlating patient's body metrics, pre-existing conditions, environmental conditions and corresponding bed position.

Some embodiments can use digital twin simulation to derive the appropriate angular adjustment or movement direction, the system further would be able to use transfer learning to simulate and improvise the learning to other patients.

In some embodiments, the system is able to accommodate nursing at home for a patient, who is suffering from impairment of the organs of movement, or at a nursing home a person, who only may move with difficulty (i.e., due to spastic paralysis, is laying) while being moved across the bed. A prerequisite for the providing of appropriate turning to prevent injury for the person may include, laying on the sheet.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether or not explicitly described.

It should be understood that the Figures are merely schematic and are not drawn to scale. It should also be understood that the same reference numerals are used throughout the Figures to indicate the same or similar parts.

FIG. 1 is a functional block diagram illustrating a patient mobility environment, designated as 100, designated as 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Patient mobility environment 100 includes network 101, IoT devices 102, smart bed 103 and digital twin server 104.

Network 101 can be, for example, a telecommunications network, a local area network (LAN), a wide area network (WAN), such as the Internet, or a combination of the three, and can include wired, wireless, or fiber optic connections. Network 101 can include one or more wired and/or wireless networks that are capable of receiving and transmitting data, voice, and/or video signals, including multimedia signals that include voice, data, and video information. In general, network 101 can be any combination of connections and protocols that can support communications between server 110, IoT devices 102, smart bed 103, digital twin server 104 and other computing devices (not shown) within patient mobility environment 100. It is noted that other computing devices can include, but is not limited to, IoT devices 102 and any electromechanical devices capable of carrying out a series of computing instructions.

IoT devices 102 can be any smart device (e.g., thermal sensors/imaging, heart rate monitor, wireless camera and microphones) that can detect real world sensory information. Furthermore, IoT devices 102 can also include wearable smart devices, smart phones, smart sensors or any other devices associated with a healthcare infrastructure.

Smart bed 103 are patient bed with multiple segmented rollers along the periphery of the bed, wherein the segmented rollers will synchronously work to move portion of the e-cloth and thereby moving the patient and/or part of the patient in 3 dimensional x-y-z axial direction. Other embodiments of smart bed 103 can include hospital or nursing home bed, wherein the beds comprises of a sheet arranged between multiple rollers along the periphery of the patient. And wherein the two opposite sides or end portions of the sheet each being wound around one of the two rollers of which each is associated with a drive roller. Other embodiments of the smart bed may include an electromotor drive, serving to rotate the rollers to wind the sheet from one or plurality of rollers to the other plurality of rollers in either direction. Specifically, the rollers provides a turning of a person/patient laying on the sheet. Based on the context of rolling of the patient, smart bed 103 can enable the multi segmented roller collaborative rolling wherein one set of roller will dispatch e-cloth in an axial direction and another set of roller will retract the smart cloth in another axial direction.

E-cloth refers to a range of smart textile products with electronic intelligence (e.g., sensors, etc.) and can react to external stimuli. Smart textiles differ from conventional textiles in regard to the capability of sensing and responding to their environment. The smart textiles can be described as materials which can sense and react to environmental conditions based on thermal, mechanical, electrical, magnetic, etc.

Smart bed 103 can be equipped with sanitization equipment that can perform a full bed cleaning and/or cleaning of the patient (while on the bed).

Digital twin server 104 can be servers used to simulate the digital twin of a patient mobility environment 100. Digital twin server 104 can communicate with IoT devices 102 and smart bed 103 to update the simulation status including modeling.

Patient 105 are users with medical conditions/ailments that require them to rely the use of beds. Patient 105 are users of the smart beds.

Server 110 and/or digital twin server 104 can be a standalone computing device, a management server, a web server, a mobile computing device, or any other electronic device or computing system capable of receiving, sending, and processing data. In other embodiments, server 110 can represent a server computing system utilizing multiple computers as a server system, such as in a cloud computing environment. In another embodiment, server 110 can be a laptop computer, a tablet computer, a netbook computer, a personal computer (PC), a desktop computer, a personal digital assistant (PDA), a smart phone, or any other programmable electronic device capable of communicating other computing devices (not shown) within patient mobility environment 100 via network 101. In another embodiment, server 110 represents a computing system utilizing clustered computers and components (e.g., database server computers, application server computers, etc.) that act as a single pool of seamless resources when accessed within patient mobility environment 100.

Embodiment of the present invention can reside on server 110 or digital twin server 104. Server 110 includes patient component 111 and database 116.

Patient component 111 provides the capability to create a classified corpus of contextual scenarios and correlating patient's body metrics, pre-existing conditions, environmental conditions and corresponding smart bed position. Patient component 111 leverages digital twin simulation based on the previous information to derive the appropriate angular adjustment or movement direction of patients 105 (via smart bed 103), the system further would be able to use transfer learning to simulate and improvise the learning to other patients.

Database 116 is a repository for data used by patient component 111. Database 116 can be implemented with any type of storage device capable of storing data and configuration files that can be accessed and utilized by server 110, such as a database server, a hard disk drive, or a flash memory. Database 116 uses one or more of a plurality of techniques known in the art to store a plurality of information. In the depicted embodiment, database 116 resides on server 110. In another embodiment, database 116 may reside elsewhere within patient mobility environment 100, provided that patient component 111 has access to database 116. Database 116 may store information associated with, but is not limited to, knowledge corpus, patient medical history, IoT devices, smart bed profile and setting, modeling of patient, patient activities and home automation routines.

Patient component 111 contains subcomponents (see FIG. 1): patient component 121, IoT component 122, digital twin component 123 and AI component 124.

As is further described herein below, patient component 121 of the present invention provides the capability of managing information associated with patient 105. Patient information can include, but it is not limited to, patient identification, medical condition of the patient, medication dosage and frequency, updated patient charts/lab results and attending physician's information.

Furthermore, patient component 121 can include the capability of managing daily activities (i.e., contextual scenarios) associated with the patient. Contextual scenarios can include, but it is not limited to, eating, drinking, cleaning, other bodily functions, medication schedule, exercise/rehabilitation and watching TV.

As is further described herein below, IoT component 122 of the present invention provides the management of information collection and instructions to various IoT devices 102. Collected information from IoT devices 102 may include, but is not limited to, person, health parameters, body position, body mass, weight of the injured portion, comfort, temperature, humidity, motion, brainwave sensors, etc. Other IoT device (e.g., smart home, etc.) information (i.e., environmental and weather condition) from the environment, may include, odor, noise, light, moisture, temperature.

Furthermore, IoT component 122 is able to interface/manage smart beds and other smart devices (non-IoT devices) such as smart home sensors, etc. For example, IoT component can manage smart bed 103, which includes the capability of interfacing to various sensors throughout the bed (e.g., position, pressure sensor, etc.) and ability to instruct the motors (i.e., rollers) of the bed (including E-Cloth) to move the patients in any three-dimensional coordinates/direction.

As is further described herein below, digital twin component 123 of the present invention provides the capability of managing IoT devices (i.e., 102), smart bed 103 and interfacing with digital twin server 104. One aspect of managing IoT devices 102, includes receiving information from various IoT devices (through IoT component 122) and incorporating/updating existing model/simulation for the patient in the digital twin environment (i.e., 104).

Another aspect of digital twin component 123 is interfacing with digital twin server 104. This means that simulations and modeling on digital twin server 104 is managed by digital twin component 123, functionality may include, but it is not limited to, creating new simulations and models based on information from IoT devices 102, patient component 121 and updating existing simulations with real-time data and forecasting new medical scenarios based on patient status.

As is further described herein below, AI component 124 of the present invention provide the optimal bed setting/profile for a patient and coordinate the movement of the patient based on the setting while minimizing any traumatic incursion with any existing medical condition. AI component 124 can initiate a simulation/model, through digital twin component 123 and based on the result, AI component 124 can instruct smart bed 103 to move the patient to certain positions based on the desired activity for the day. Other aspects of AI component 124 may include modeling of patients for transporting from one bed to another bed (i.e., not necessary in one location).

Figure 2:
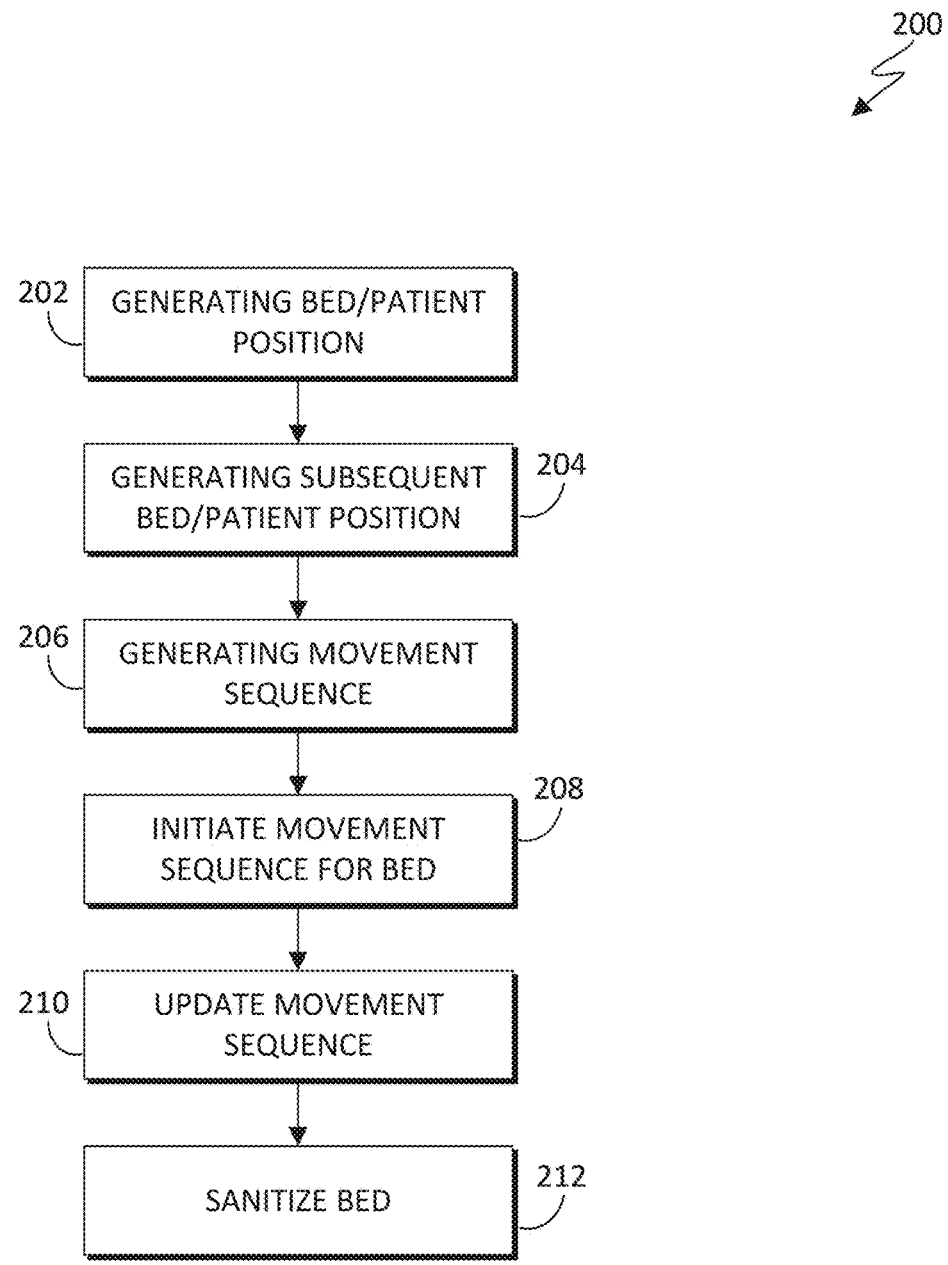
FIG. 2 is a high-level flowchart illustrating the operation of patient component 111, designated as 200, in accordance with an embodiment of the present invention.

FIG. 2 is a high-level flowchart illustrating the operation of patient component 111, designated as 200, in accordance with one embodiment of the present invention.

Patient component 111 generates initial bed/patient position (step 202). In an embodiment, patient component 111, through AI component 124, generates various patient bed/lying positions based on the digital twin copy of the patient. The bed positions may include the following, non-compliant position, degree of non-compliances, pain modeling in one/many portions of patient, one/more bed bedsores/pressure ulcers, the time period of lying in one position and stress.

Patient component 111 generates subsequent bed/patient position (step 204). In an embodiment, patient component 111, generates the patient desired/secondary and/or tertiary bed/lying position based on context, sensor data and the need for patient movement.

Patient component 111 generates movement sequence (step 206). In an embodiment, patient component 111, generates a sequence of movement based on, but it not limited to, context, sensor data, and desired position.

Patient component 111 initiates movement sequence for bed (step 208). In an embodiment, patient component 111, initiates the triggers the bed rollers to achieve the desired roll based on the 3D rolling profile for the patient.

Patient component 111 updates movement sequence (step 210). In an embodiment, patient component 111, dynamically adjusts the movement sequence based on new information. Information can include, but it is not limited to, new patient position, weather, patients condition (i.e., skin conditions from e-cloth sensor), sweating, and other data from the digital twin simulation.

Patient component 111 sanitizes the bed (step 212). In an embodiment, patient component 111, disinfectants/sanitizes the bed using e-cloth based triggers and/or based on digital twin simulation.

Figure 3:
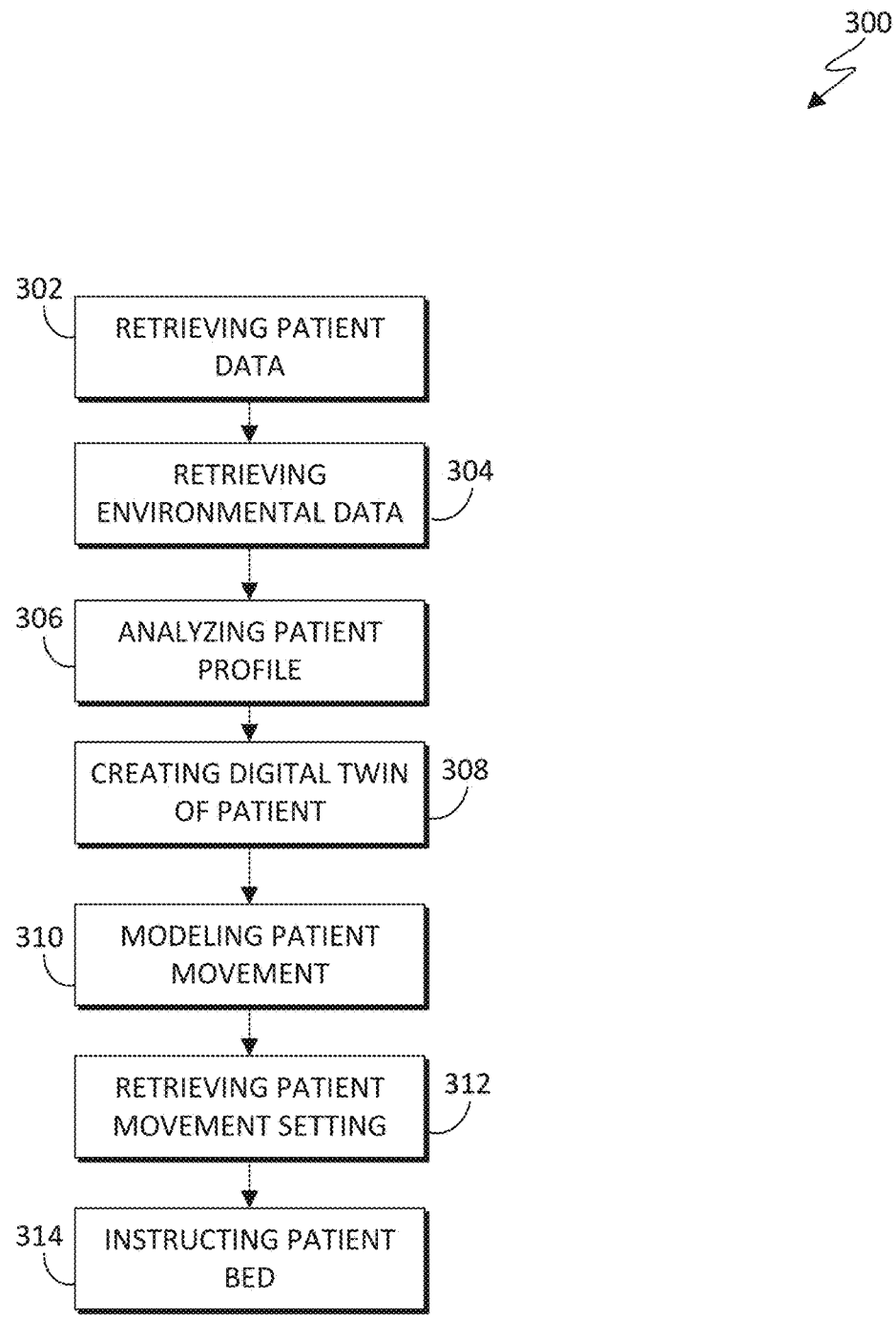
FIG. 3 is a high-level flowchart illustrating the operation of patient component 111, designated as 300, in accordance with another embodiment of the present invention.

FIG. 3 is a high-level flowchart illustrating the operation of patient component 111, designated as 300, in accordance with another embodiment of the present invention.

Patient component 111 retrieves patient data (step 302). In an embodiment, patient component 111, through patient component 121, retrieves data associated with a patient (i.e., patient 105). Patient data can include, but it is not limited to, patient identification, medical condition of the patient, medication dosage and frequency, updated patient charts/lab results and attending physician's information. An example will be used to illustrate the steps. For example, patient_A, has undergone spinal surgery is immobile for at least month. Patient_A weighs 350 pounds. At least three time per day, patient_A, requires to be repositioned to with the face down per doctor's order. Patient_A is laying on a smart bed, bed_A. Bed_A has three-dimensional axis roller/motors and e-cloths.

Patient component 111 retrieves environmental data (step 304). In an embodiment, patient component 111, through IoT component 122, retrieved various data, such as environmental data, IoT device 102 data and data from smart bed 103. Environmental data can include odor, noise, light, moisture and temperature. Other data from IoT device 102 can include health data such as health parameters (e.g., blood pressure, heartbeat, etc.), body position, comfort level, temperature, and humidity, motion and brainwave sensor. Data from smart bed 103 can include, body position, body mass and weight of the injured portion. In continuing with the prior example, data related to patient_A, can include the position of the patient (patient is lying on his back in the middle of the bed), heart rate and blood pressure is normal, the temperature of the room is 71° F., humidity is within acceptable human range and no known external pressure on the spine of patient_A.

Patient component 111 analyzes patient profile (step 306). In an embodiment, patient component 111, through AI component 124, analyzes the data related to the patient and goals/restriction/requirements from the medical staff (i.e., doctor). These goals/restrictions are unique to each patient and the accompanying medical conditions. Patient component 111 attempts to create an initial patient bed profile based on the data and medical restrictions. In continuing with the prior example, patient_A is required to be repositioned to his stomach at least three times a day. Bed profile are settings for the smart beds to keep patient at a desired position. Bed profiles (e.g., initial bed profile, daily bed profile, resting bed profile, etc.) are continuously adjusted based on feedback from IoT devices 102 and/or AI component 124.

Patient component 111 creates digital twin of patient (step 308). In an embodiment, patient component 111, through digital twin component 123, creates a digital twin of the patient. In continuing with the prior example, a digital twin of patient_A is created on digital twin server 104.

Patient component 111 models patient movement (step 310). In an embodiment, patient component 111, through AI component 124, simulates patient movement (on digital twin server 104) based on the medical requirements/parameters. Based on the result of the simulation, a patient movement setting (via instructions for a smart bed) is generated.

In other embodiments, patient component 111 may model/simulate patient movement not based on a requirement/restriction from a healthcare professional. For example, certain medical symptoms develops when a patient lies in one position for too long. These pressure-related symptoms, such as ulcer can be alleviated by simulating the frequency and body part movement by digital twin patient counterpart. Some embodiments may be able to identify prolonged lying in one position for prolonged time period and will be able to dynamically change patient's lying profile to a secondary position using differential time based patient movement and auto triggering to a tertiary position an elapsed time frame.

Some embodiments, based on potential condition of pressure ulcer in one or many portions of the body due to patient lying in one position for prolonged time period, the embodiment will be able to dynamically change patient's lying profile to a secondary position using differential time based patient movement and auto triggering to a tertiary position an elapsed time frame.

Some embodiments can be able to identify potential uncomfortable scenarios (skin irritants, frequent sweating, moist skin) generating a need of patient movement or re-adjustment to prevent the possible conditions.

Some embodiments can auto initiate smart home based events to adjust the environmental conditions like but not limited to auto adjustment of the humidity and temptation, auto opening or closure of smart windows, auto dimming of bright light, etc. thereby creating an environmental scenario comforting to the patient condition.

Patient component 111 retrieves patient movement setting (step 312). In an embodiment, patient component 111, through AI component 124, retrieves the bed setting/instructions based on the simulation and modeling. In continuing with the example related to patient_A, one or more bed setting for bed_A, is retrieved based on the result of the simulation for patient_A.

Patient component 111 coordinates smart bed (step 314). In an embodiment, patient component 111, through IoT component 122, instructs the smart bed to move the patient based on the bed setting. In continuing with the example related to patient_A, the one or more retrieved bed setting for bed_A, is executed on bed_A for patient_A. Patient_A is repositioned on his stomach in the morning time based on the recommendation from the healthcare provider. It is noted that the patient can be repositioned automatically should there be any indication of discomfort or issues (via IoT devices monitoring the vital symptoms of the patient). Any feedback form the patient and/or IoT devices can be further update to the existing digital twin copy on the digital twin server.

Figure 4:
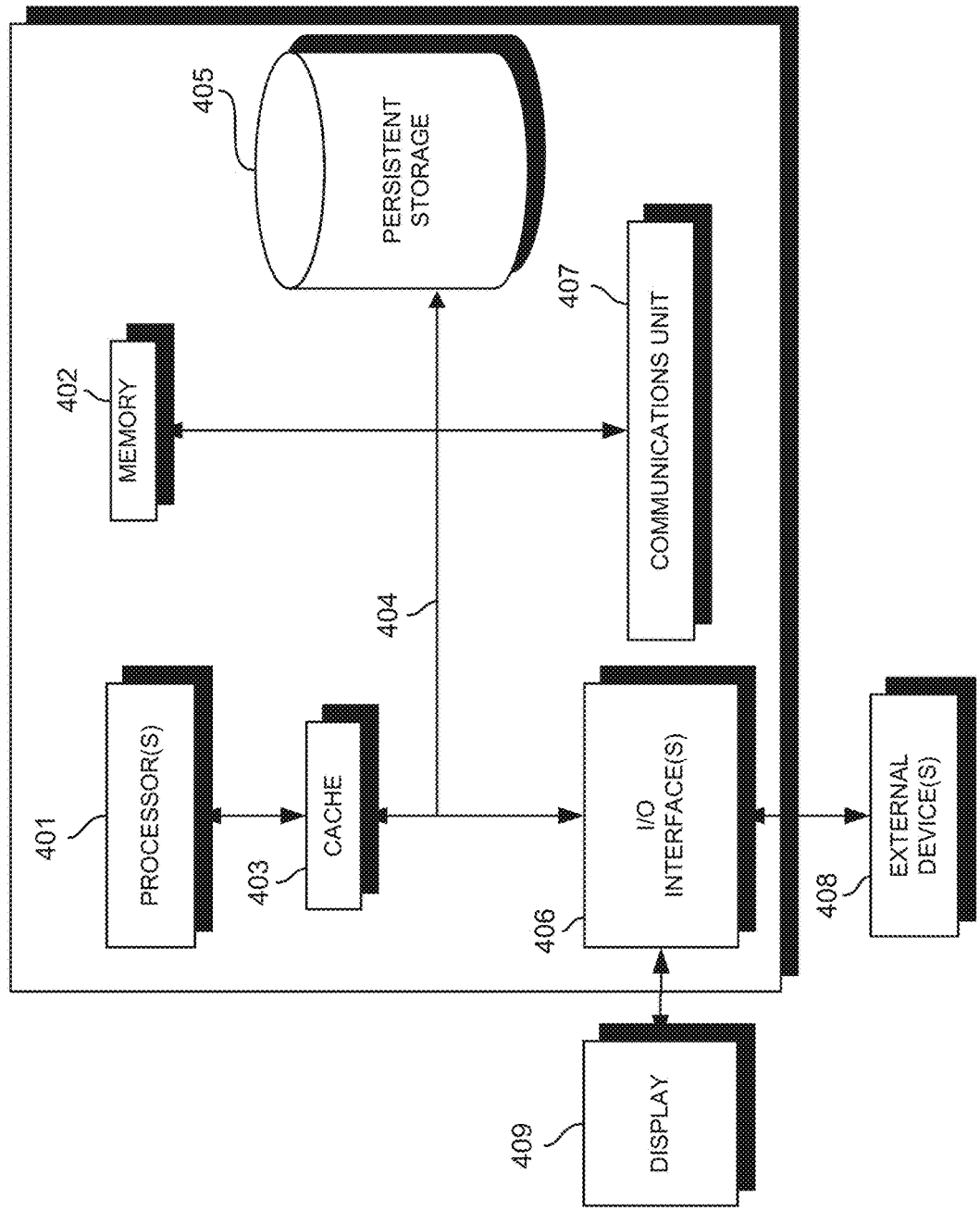
FIG. 4 depicts a block diagram, designated as 400, of components of a server computer capable of executing the patient component 111 within the patient mobility environment 100, in accordance with an embodiment of the present invention.

FIG. 4, designated as 400, depicts a block diagram of components of patient component 111 application, in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

FIG. 4 includes processor(s) 401, cache 403, memory 402, persistent storage 405, communications unit 407, input/output (I/O) interface(s) 406, and communications fabric 404. Communications fabric 404 provides communications between cache 403, memory 402, persistent storage 405, communications unit 407, and input/output (I/O) interface(s) 406. Communications fabric 404 can be implemented with any architecture designed for passing data and/or control information between processors (such as microprocessors, communications and network processors, etc.), system memory, peripheral devices, and any other hardware components within a system. For example, communications fabric 404 can be implemented with one or more buses or a crossbar switch.

Memory 402 and persistent storage 405 are computer readable storage media. In this embodiment, memory 402 includes random access memory (RAM). In general, memory 402 can include any suitable volatile or non-volatile computer readable storage media. Cache 403 is a fast memory that enhances the performance of processor(s) 401 by holding recently accessed data, and data near recently accessed data, from memory 402.

Program instructions and data (e.g., software and data x10) used to practice embodiments of the present invention may be stored in persistent storage 405 and in memory 402 for execution by one or more of the respective processor(s) 401 via cache 403. In an embodiment, persistent storage 405 includes a magnetic hard disk drive. Alternatively, or in addition to a magnetic hard disk drive, persistent storage 405 can include a solid state hard drive, a semiconductor storage device, a read-only memory (ROM), an erasable programmable read-only memory (EPROM), a flash memory, or any other computer readable storage media that is capable of storing program instructions or digital information.

The media used by persistent storage 405 may also be removable. For example, a removable hard drive may be used for persistent storage 405. Other examples include optical and magnetic disks, thumb drives, and smart cards that are inserted into a drive for transfer onto another computer readable storage medium that is also part of persistent storage 405. Patient component 111 can be stored in persistent storage 405 for access and/or execution by one or more of the respective processor(s) 401 via cache 403.

Communications unit 407, in these examples, provides for communications with other data processing systems or devices. In these examples, communications unit 407 includes one or more network interface cards. Communications unit 407 may provide communications through the use of either or both physical and wireless communications links. Program instructions and data (e.g., patient component 111) used to practice embodiments of the present invention may be downloaded to persistent storage 405 through communications unit 407.

I/O interface(s) 406 allows for input and output of data with other devices that may be connected to each computer system. For example, I/O interface(s) 406 may provide a connection to external device(s) 408, such as a keyboard, a keypad, a touch screen, and/or some other suitable input device. External device(s) 408 can also include portable computer readable storage media, such as, for example, thumb drives, portable optical or magnetic disks, and memory cards. Program instructions and data (e.g., patient component 111) used to practice embodiments of the present invention can be stored on such portable computer readable storage media and can be loaded onto persistent storage 405 via I/O interface(s) 406. I/O interface(s) 406 also connect to display 409.

Display 409 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

The corresponding structures, materials, acts, and equivalents of all means or steps plus function elements in the claims below are intended to include any structure, material, or act for performing the function in combination with other claimed elements, as specifically claimed. The description of the present invention has been presented for purposes of illustration and description, but is not intended to be exhaustive or limited to the invention in the form disclosed. Many modifications and variations will be apparent to those of ordinary skills in the art without departing from the scope and spirit of the invention. The embodiments are chosen and described in order to best explain the principles of the invention and the practical application, and to enable others of ordinary skills in the art to understand the invention for various embodiments with various modifications, as are suited to the particular use contemplated.

Finally, the proposed concept may be summarized in a nutshell in the following clauses:

1. The proposed system is an AI infused patient rolling which determines the need for patient positional adjustment based on the context, IOT sensor data and patient health conditions and thereby initiates dynamic three dimensional rolling profile for the patient with applied AI capabilities.
2. The proposed system would enable three dimensional rolling of the patient using multiple segmented rollers along the periphery of the bed wherein the segmented rollers will synchronously work to move portion of the e-cloth and thereby moving the patient and/or part of the patient in 3 dimensional x-y-z axial direction.
3. Based on the context of rolling of the patient, the proposed system will enable the multi segmented roller collaborative rolling wherein one set of roller will dispatch e-cloth in an axial direction and another set of roller will retract the smart cloth in another axial direction.
4. The proposed system will be able to determine a non-complaint position and degree of non-complaint of the patient and contextual situation (type of and part of wound or infection or fracture, IV drip in hand etc.) thereby the proposed system will auto initiate the axial rolling to reset the patient to its original position based on the patients auto sliding to another non-compliant position (ex: during an inclined lying condition).
5. Based on the pain modelling (back pain, fracture, muscle stiffness, cramps etc.) in one or many portions of the body due to patient lying in one position for prolonged time period, the proposed system will be able to dynamically change patient's lying profile to a secondary position to relieve stress and pressure from the portion of the body with pain.
6. The proposed system while doing the autonomous 3D movement for patients, it take the near-real-time IoT feedback of the pain and body stress causing due to particular movement, based on this the proposed system will suggest the immediately the alternative movement that might reduce/relief the pain/stress caused.
7. Using multifarious IoT sensor data from smart wearables and e-cloth, the proposed system will dynamically be able to detect a condition for patient pressure ulcer, and thereby auto initiate the patient and/or portion of the patient's body movement by triggering of rolling for the segmented roller releasing e-cloth in an axial direction to relieve the pressure from an ulcer prone part of the patient's body.

The proposed system will be able to dynamically change patient's lying profile to a secondary position using differential time based patient movement and auto triggering to a tertiary position an elapsed time frame.
8. Based on the environmental and whether condition odor, noise, light, moisture, temperature etc.), the system model patients digital twin thereby simulating with the environmental and whether conditions to identify potential uncomfortable scenarios (skin irritants, frequent sweating, moist skin) generating a need of patient movement or re-adjustment to prevent the possible conditions.

The system further auto initiates smart home based events to adjust the environmental conditions like but not limited to auto adjustment of the humidity and temptation, auto opening or closure of smart windows, auto dimming of bright light etc. thereby creating an environmental scenario comforting to the patient condition.
9. The proposed system will autonomously initiate anti disinfectant for any portion of the patient's body predicted to be infecting like wound, pressure ulcer etc. and thereby the smart or e-cloth would auto dispense disinfectant agent to the portion of the body.
10. The proposed system will be able to generate a position profiling based on time duration and auto initiate patient movement after the expiry of primary time duration and its corresponding position to a secondary position for a secondary period of time, wherein the system also checks the movement accuracy based on patient weight etc., and thereby initiates an adjustment movement for any inaccurate positioning.
11. The proposed system further assess the patient's current health profile and identify the required movement of specific body part in certain health situation which is necessary to improvise the condition or to derive the current fact, and further predict the 3D movement which autonomously delivered by the Smart bedding system.
12. The proposed system will be able to autonomously adjust the positioning of the patient by dynamically setting the patient movement based on IOT and smart wearable based identification of potential pulmonary congestion due to mucus and/fluid build-up in chest for multifarious reasons like but too limited to bloating, overeating, inability to swallow, or pre-existing pulmonary conditions.
13. The proposed system will be able to create a classified corpus of contextual scenarios and correlating patient's body metrics, pre-existing conditions, environmental conditions and corresponding bed position and thereby would use digital twin simulation to derive the appropriate angular adjustment or movement direction, the system further would be able to use transfer learning to simulate and improvise the learning to other patients.
14. The proposed system on deriving the patient current health situation, leveraging the classified corpus data, it also suggests the surrounded IoT enabled resource availability requirement around patient bedding system and generate required care plan.
15. The method includes a step of providing an AI infused patient rolling system which determines the need for patient positional adjustment based on the context, IOT sensor data and patient health conditions and thereby initiates dynamic three dimensional rolling profile for the patient with applied AI capabilities.

16. The method includes a step wherein, the system would enable three dimensional rolling of the patient using multiple segmented rollers along the periphery of the bed wherein the segmented rollers will synchronously work to move portion of the e-cloth and thereby moving the patient and/or part of the patient in 3 dimensional x-y-z axial direction.

17. The method includes a step wherein, based on the context of rolling of the patient, the system will enable the multi segmented roller collaborative rolling wherein one set of roller will dispatch e-cloth in an axial direction and another set of roller will retract the smart cloth in another axial direction.

18. The method includes a step wherein, the system will be able to determine a non-complaint position and degree of non-complaint of the patient and contextual situation (type of and part of wound or infection or fracture, IV drip in hand etc.) thereby the system will auto initiate the axial rolling to reset the patient to its original position based on the patients auto sliding to another non-compliant position (ex: during an inclined lying condition).

19. The method includes a step wherein, based on the pain modelling (back pain, fracture, muscle stiffness, cramps etc.) in one or many portions of the body due to patient lying in one position for prolonged time period, the system will be able to dynamically change patient's lying profile to a secondary position to relieve stress and pressure from the portion of the body with pain.

20. The method includes a step wherein, the system while doing the autonomous 3D movement for patients, takes the near-real-time IoT feedback of the pain and body stress causing due to particular movement, based on this the system will suggest immediately the alternative movement that might reduce/relief the pain/stress caused.

21. The method includes a step wherein by using multifarious IOT sensor data from smart wearables and e-cloth, the system will dynamically be able to detect a condition for patient pressure ulcer, and thereby auto initiate the patient and/or portion of the patient's body movement by trigging of rolling for the segmented roller releasing e-cloth in an axial direction to relieve the pressure from an ulcer prone part of the patient's body.

22. The method includes a step wherein, the system will be able to dynamically change patient's lying profile to a secondary position using differential time based patient movement and auto triggering to a tertiary position an elapsed time frame.

23. The method includes a step wherein, based on the environmental and weather condition (odor, noise, light, moisture, temperature etc.), the system model patients digital twin thereby simulating with the environmental and whether conditions to identify potential uncomfortable scenarios (skin irritants, frequent sweating, moist skin) generating a need of patient movement or re-adjustment to prevent the possible conditions.

24. The method includes a step wherein, the system further auto initiates smart home based events to adjust the environmental conditions like but not limited to auto adjustment of the humidity and temperature, auto opening or closure of smart windows, auto dimming of bright light etc. thereby creating an environmental scenario comforting to the patient condition.

25. The method includes a step wherein, the system will autonomously initiate anti disinfectant for any portion of the patient's body predicted to be infecting like wound, pressure ulcer etc. and thereby the smart or e-cloth would auto dispense disinfectant agent to the portion of the body.

26. The method includes a step wherein, the system will be able to generate a position profiling based on time duration and auto initiate patient movement after the expiry of primary time duration and its corresponding position to a secondary position for a secondary period of time, wherein the system also checks the movement accuracy based on patient weight etc., and thereby initiates an adjustment movement for any inaccurate positioning.

27. The method includes a step wherein, the system further assesses the patient's current health profile and identify the required movement of specific body part in certain health situation which is necessary to improvise the condition or to derive the current fact, and further predict the 3D movement which autonomously delivered by the Smart bedding system.

28. The method includes a step wherein, system will be able to autonomously adjust the positioning of the patient by dynamically setting the patient movement based on IOT and smart wearable based identification of potential pulmonary congestion due to mucus and/fluid build-up in chest for multifarious reasons like but too limited to bloating, overeating, inability to swallow, or pre-existing pulmonary conditions.

29. The method includes a step wherein, system will be able to create a classified corpus of contextual scenarios and correlating patient's body metrics, pre-existing conditions, environmental conditions and corresponding bed position and thereby use digital twin simulation to derive the appropriate angular adjustment or movement direction, the system further would be able to use transfer learning to simulate and improvise the learning to other patients.

30. The method includes a step wherein, the system on deriving the patient current health situation, leveraging the classified corpus data, it also suggests the surrounded IoT enabled resource availability requirement around patient bedding system and generate required care plan.

What is claimed is:

1. A computer-implemented method for providing movement settings for a smart bed associated with an immobile patient, the computer-implemented method comprising:
    retrieving patient data associated with a patient;
    retrieving environmental and health data associated with the patient;
    analyzing patient profile associated with the patient;
    creating digital twin version of the patient associated with a patient bed, wherein the patient bed is a smart bed equipped with IoT components, plurality of motors, plurality of segmented rollers attached to E-cloths and sensors and based on the environment and health data, the patient data, patient profile and health data;
    modeling mobility of the patient based on the digital twin version of the patient and determining, using the digital twin version of the patient, an optimal compliant setting to assist with the mobility of the patient and the optimal compliant setting includes one or more settings for the patient bed that minimizes any traumatic incursion with any existing medical conditions associated with the patient and is based on a desired activity of the patient, wherein the desired activity includes, at least, sitting, sleeping, exercise and intake of medication and eating;
    retrieving the optimal compliant setting from the digital twin version of the patient; and
    instructing the patient bed to re-position, via the plurality of segmented rollers which can retract or dispatch the E-cloths in, at least, three axial directions, the patient based on the optimal compliant and a desired activity of the patient.

2. The computer-implemented method of claim 1, wherein patient data, further comprises of patient identification, medical condition of the patient, medication dosage and frequency, updated patient charts/lab results and attending physician's information.

3. The computer-implemented method of claim 1, wherein environmental data, further comprises of odor, noise, light, moisture and temperature and health data further comprises of health parameters, body position, comfort level, temperature, and humidity, motion and brainwave sensor data.

4. The computer-implemented method of claim 1, wherein analyzing patient profile, further comprises:
creating initial patient bed profile based on patient data, environmental data and medical restrictions.

5. The computer-implemented method of claim 1, wherein creating digital twin version of patient is based on patient data and environment data.

6. The computer-implemented method of claim 1, wherein modeling patient movement is based on medical requirements/parameters.

7. The computer-implemented method of claim 1, wherein instructing a patient bed is based on the patient movement setting.

8. A computer program product for providing movement settings for a smart bed associated with an immobile patient, the computer program product comprising:
one or more computer readable storage media and program instructions stored on the one or more computer readable storage media, the program instructions comprising:
program instructions to retrieve patient data associated with a patient;
program instructions to retrieve environmental and health data associated with the patient;
program instructions to analyze patient profile associated with the patient;
program instructions to create digital twin version of the patient associated with a patient bed, wherein the patient bed is a smart bed equipped with IoT components, plurality of motors, plurality of segmented rollers attached to E-cloths and sensors and based on the environment and health data, the patient data, patient profile and health data;
program instructions to model mobility of the patient based on the digital twin version of the patient and determining, using the digital twin version of the patient, an optimal compliant setting to assist with the mobility of the patient and the optimal compliant setting includes one or more settings for the patient bed that minimizes any traumatic incursion with any existing medical conditions associated with the patient and is based on a desired activity of the patient, wherein the desired activity includes, at least, sitting, sleeping, exercise and intake of medication and eating;
program instructions to retrieve the optimal compliant setting from the digital twin version of the patient; and
program instructions to instruct the patient bed to re-position, via the plurality of segmented rollers which can retract or dispatch the E-cloths in, at least, three axial directions, the patient based on the optimal compliant and a desired activity of the patient.

9. The computer program product of claim 8, wherein patient data, further comprises of patient identification, medical condition of the patient, medication dosage and frequency, updated patient charts/lab results and attending physician's information.

10. The computer program product of claim 8, wherein environmental data, further comprises of odor, noise, light, moisture and temperature and health data further comprises of health parameters, body position, comfort level, temperature, and humidity, motion and brainwave sensor data.

11. The computer program product of claim 8, wherein program instructions to analyze patient profile, further comprises:
program instructions to create initial patient bed profile based on patient data, environmental data and medical restrictions.

12. The computer program product of claim 8, wherein program instructions to create digital twin version of patient is based on patient data and environment data.

13. The computer program product of claim 8, wherein program instructions to model patient movement is based on medical requirements/parameters.

14. The computer program product of claim 8, wherein program instructions to instruct a patient bed is based on the patient movement setting.

15. A computer system for providing movement settings for a smart bed associated with an immobile patient, the computer system comprising:
one or more computer processors;
one or more computer readable storage media; and
program instructions stored on the one or more computer readable storage media for execution by at least one of the one or more computer processors, the program instructions comprising:
program instructions to retrieve patient data associated with a patient;
program instructions to retrieve environmental and health data associated with the patient;
program instructions to analyze patient profile associated with the patient;
program instructions to create digital twin version of the patient associated with a patient bed, wherein the patient bed is a smart bed equipped with IoT components, plurality of motors, plurality of segmented rollers attached to E-cloths and sensors and based on the environment and health data, the patient data, patient profile and health data;
program instructions to model mobility of the patient based on the digital twin version of the patient and determining, using the digital twin version of the patient, an optimal compliant setting to assist with the mobility of the patient and the optimal compliant setting includes one or more settings for the patient bed that minimizes any traumatic incursion with any existing medical conditions associated with the patient and is based on a desired activity of the patient, wherein the desired activity includes, at least, sitting, sleeping, exercise and intake of medication and eating;
program instructions to retrieve the optimal compliant setting from the digital twin version of the patient; and
program instructions to instruct the patient bed to re-position, via the plurality of segmented rollers which can retract or dispatch the E-cloths in, at least, three axial directions, the patient based on the optimal compliant and a desired activity of the patient.

16. The computer system of claim 15, wherein patient data, further comprises of patient identification, medical condition of the patient, medication dosage and frequency, updated patient charts/lab results and attending physician's information.

17. The computer system of claim 15, wherein environmental data, further comprises of odor, noise, light, moisture and temperature and health data further comprises of health parameters, body position, comfort level, temperature, and humidity, motion and brainwave sensor data.

18. The computer system of claim 15, wherein program instructions to analyze patient profile, further comprises:
   program instructions to create initial patient bed profile based on patient data, environmental data and medical restrictions.

19. The computer system of claim 15, wherein program instructions to create digital twin version of patient is based on patient data and environment data.

20. The computer system of claim 15, wherein program instructions to model patient movement is based on medical requirements/parameters.

\* \* \* \* \*